(12) United States Patent
Régnier et al.

(10) Patent No.: US 9,743,852 B2
(45) Date of Patent: Aug. 29, 2017

(54) ATRAUMATIC DETECTION/STIMULATION MICROLEAD

(71) Applicant: SORIN CRM SAS, Clamart (FR)

(72) Inventors: Willy Régnier, Longjumeau (FR); Nicolas Shan, Antony (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 15/048,841

(22) Filed: Feb. 19, 2016

(65) Prior Publication Data

US 2016/0166163 A1    Jun. 16, 2016

Related U.S. Application Data

(62) Division of application No. 14/052,430, filed on Oct. 11, 2013, now Pat. No. 9,265,864.

(30) Foreign Application Priority Data

Oct. 12, 2012    (FR) ...................................... 12 59759

(51) Int. Cl.
| | | |
|---|---|---|
| *A61N 1/00* | (2006.01) | |
| *A61B 5/04* | (2006.01) | |
| *A61N 1/05* | (2006.01) | |
| *A61L 31/00* | (2006.01) | |
| *C09J 5/00* | (2006.01) | |
| *C09J 183/04* | (2006.01) | |

(52) U.S. Cl.
CPC .............. *A61B 5/04* (2013.01); *A61L 31/005* (2013.01); *A61N 1/05* (2013.01); *A61N 1/056* (2013.01); *C09J 5/00* (2013.01); *A61B 2562/125* (2013.01); *A61N 1/0568* (2013.01); *A61N 2001/0585* (2013.01); *C09J 183/04* (2013.01); *C09J 2400/163* (2013.01); *C09J 2483/00* (2013.01); *Y10T 29/49224* (2015.01)

(58) Field of Classification Search
USPC ...................................................... 607/122
See application file for complete search history.

(56) References Cited

U.S. PATENT DOCUMENTS

| | | |
|---|---|---|
| 4,531,943 A | 7/1985 | Van Tassel et al. |
| 4,934,049 A | 6/1990 | Kiekhafer et al. |
| | (Continued) | |

FOREIGN PATENT DOCUMENTS

| | | |
|---|---|---|
| EP | 2 455 131 A1 | 5/2012 |
| FR | 2550454 a1 | 2/1985 |

OTHER PUBLICATIONS

Preliminary Search Report for French Patent Application No. FR1259759, dated Feb. 12, 2013, 2 pages.

*Primary Examiner* — Nicole F Johnson
(74) *Attorney, Agent, or Firm* — Foley & Lardner LLP

(57) ABSTRACT

An atraumatic detection/stimulation lead is disclosed. The lead includes at least one microcable having a core cable comprising a plurality of elementary metal strands. One of the microcables has provided at its distal end an atraumatic protection device. The atraumatic protection device includes a protective coating on the distal ends of the elementary strands of the microcable, and the protective coating is covered by a protective cap of deformable material. The protective cap may be a conical distal end adapted to deform and axially flatten out. The microcable may have an overall diameter less than or equal to 1.5 French (0.50 mm).

20 Claims, 3 Drawing Sheets

(56) References Cited

U.S. PATENT DOCUMENTS

| | | |
|---|---|---|
| 6,192,280 B1 | 2/2001 | Sommer et al. |
| 7,047,082 B1 | 5/2006 | Schrom et al. |
| 7,761,170 B2 * | 7/2010 | Kaplan ................. A61N 1/056 |
| | | 600/372 |
| 8,521,306 B2 | 8/2013 | Ollivier |
| 2002/0099430 A1 * | 7/2002 | Verness ................. A61N 1/056 |
| | | 607/122 |
| 2006/0089691 A1 | 4/2006 | Kaplan et al. |
| 2012/0130464 A1 | 5/2012 | Ollivier |

* cited by examiner

ATRAUMATIC DETECTION/STIMULATION MICROLEAD

CROSS-REFERENCE TO RELATED APPLICATIONS

This application is a divisional of U.S. application Ser. No. 14/052,430, filed Oct. 11, 2013, which claims the benefit of and priority to French Patent Application No. 1259759, filed Oct. 12, 2012, both of which are hereby incorporated by reference herein in their entireties.

BACKGROUND

The invention generally relates to the "active implantable medical devices" as defined by Directive 90/385/EEC of 20 Jun. 1990 the Council of the European Communities. This definition includes, in particular cardiac implants that monitor cardiac activity and generate stimulation, defibrillation or resynchronization pulses, in case of arrhythmia detected by the device. It also includes the neurological devices, the cochlear implants, the drug pumps, implanted the biological sensors, etc.

These devices comprise a housing generally designated as the "generator", electrically and mechanically connected to one or more intracorporeal "leads" provided with electrodes coming into contact with the tissues to which it is desired to apply stimulation pulses and/or collect an electrical signal: myocardium, nerve, muscle.

The present invention more specifically relates to a detection/stimulation microlead for implantation in venous, arterial and lymphatic networks.

The current principle of electrical stimulation uses a device, usually called "lead", which is implanted through various venous, arterial or lymphatic vessels, the function of which is to transmit an electrical signal to the target tissue while maintaining the following general properties:

Ease of implantation by the physician in a network of vessels of the patient, and especially easy: to advance the lead into the vessels by pushing, to make the lead follow tortuous branches and pass routes, and transmit torques;

X-ray visibility to allow the physician easy navigation through the network vessels under X rays;

Atraumaticity of the lead in blood vessels, which requires a flexible structure and the absence of rigid transition or sharp edges;

Ability to transmit an electrical signal to the tissues and to stably perform monopolar or multipolar electrical measurements;

Biocompatibility with living tissues to allow long-term implantation tissue;

Biostability, especially corrosion resistance in the living environment and resistance to mechanical stress fatigue related to patient movement and organs;

Ability to withstand sterilization (gamma rays, temperature . . . ) without damage; and Compatibility with MRI imaging, particularly important in neurology.

The current architecture of the known leads meeting these requirements can be reduced to a generally hollow structure allowing the passage of a stylet or a guidewire, and comprising components such as insulated conductor cables connected to mechanical electrodes to ensure electrical conductivity, radiopacity, etc. These leads therefore require complex assembly of a large number of parts, of associated wires and insulating parts, creating significant risk of breakage due to long term mechanical stresses to which they are exposed. Examples of such leads are given in U.S. Pat. No. 6,192,280 A and U.S. Pat. No. 7,047,082 A.

Among the difficulties encountered, the management of stiffness gradients related to the mechanical parts used can be cited, which strongly affect the implantability properties and mechanical strength in the long term (fatigue). Other problems may also arise in terms of fatigue assemblies. Indeed, any stiffness transition zone may induce risks of fatigue, difficulty to sterilize due to the presence of areas of difficult access, and problems of mechanical resistance of conductor junctions at the connection with the electrodes and the connector.

Moreover, the clinical trend in the field of implantable leads is to reduce the size to make them less invasive and easier to handle through the vessels. The current size of implantable leads is typically of the order of 4 to 6 Fr (1.33 to 2 mm). However, it is clear that reducing the size of the leads would increase complexity and impose technical constraints generating risks. However, such a reduction to less than 1.5 French (0.5 mm) or 1 French (0.33 mm), for example, open up prospects for medical applications in various fields, ranging from cardiology to neurology in the presence of a venous, arterial or even lymphatic network, such as the cerebral venous network or the coronary sinus venous network.

Today, the technology of electrical stimulation has led to major advances in the field of neuromodulation, which is to stimulate target areas of the brain for treatment of Parkinson's disease, epilepsy and other neurological diseases. One could imagine, with this type of technology, to address new areas difficult to reach today, by small pacing leads or "microleads", with great strength to ensure long-term biostability. With small microleads, it is notably possible to consider the passage in deep coronary vessels to disclose for example a device for stimulation of the left ventricle via two distinct areas. Such a technique would also allow a less invasive approach and especially superior efficacy of these treatments.

It would also be possible to connect one or more microleads through the vessel network considered to the target location. Their implantation could be done, because of their small size, by guiding devices currently used in interventional neuroradiology for the release of springs (coils) in the treatment of intracranial aneurysms. In particular, microleads of 1.5 French would allow the use of implantable catheters of an inner diameter of 1.6 French.

With particular regard to the resynchronization of the cardiac rhythm, left leads currently used are placed in or at the entrance of the coronary sinus because the progression is difficult and often limited by the gradual reduction of the diameter of the sinus passage. Monopolar microleads with a section below 1 French or multipolar microleads whose microcables' diameter is also less than 1 French open new opportunities for physicians to consider implanting beyond the coronary sinus and to position the stimulation electrodes in the deep coronary vessels of the left heart.

EP 2455131 A1 and its US counterpart U.S. Pat. No. 8,521,306 (Sorin CRM SAS) disclose a lead constituted in its active distal part by a microcable having a diameter of about 0.5 to 2 French (0.17 to 0.66 mm). This microcable comprises an electrically conductive core cable formed by a strand of a plurality of composite strands, with a polymer insulation layer partially surrounding the core cable and punctually exposed so as to expose the microcable in one or more points constituting an array of electrodes connected in series, the free end of the strand being also provided with a reported distal electrode. This configuration allows multiplication of the points of stimulation in a deep area of the coronary network.

However, this leads to new technical problems. In particular, the veins of the coronary arteries have a very narrow section, and are consequently very thin, thus inducing a risk of perforation by the microleads having a microcable structure. In addition, during manufacturing, various irregularities (hurtful edges, pointy strands, out of isodiameter strands, etc.) are met in the zone the microcable is cut (using a cutter or laser shot) at the distal end of the strands, irregularities which all are potential sources of damage to the vein walls. These leads must thus have the least traumatic possible distal end for the veins during implantation and during the life of the patient. In addition, the cardiac movements (diastole, systole) impose different constraints, by friction or compression of the lead on the venous walls. The risk is perforation of the vein and/or of the pericardial sac possibly causing serious bleeding for the patient.

In another context, the FR 2550454 A1 describes a hollow catheter for injection of contrast. The open free end of the catheter has a peripheral edge with a deformable annular balloon bag or otherwise, to avoid too sudden contact between the end of the flexible catheter sheath and the tissues of the organ where the catheter is inserted.

SUMMARY

According to the invention, provided with these objects in mind is a detection/stimulation microlead for implantation in venous, arterial and lymphatic networks, and having at least one microcable of an overall diameter of not more than 1.5 French (0.50 mm) comprising an electrically conductive core cable, formed by at least one strand of a plurality of individual wire strands.

This microlead is remarkable in that the core cable has a distal end provided with an atraumatic protection device comprising a coating means of the distal ends of the elementary strands of the core cable, and a protection cap in a both deformable and incompressible material, enveloping the coating means.

The invention is directed to both a monopolar lead with one microcable atraumatic protection of which is carried by the core cable of the microcable of the microlead and a multipolar lead formed by a strand of a plurality of microcables the atraumatic device protection of which is carried by the core cable of a microcable of the microlead located distally.

Thus, with microleads according to the invention, the reduced diameter of the single microcable or in distal position allows to reach veins of a very small section, less than 1 French, including deep veins of the coronary arteries, without the risk of perforation.

Indeed, the risk of perforation of the vessel by an edge or a metal strand of the core cable is removed by the presence of the coating means of the strands that ensures the homogeneity of the distal end of the microcable.

Furthermore, to solve problems related to the risk of perforation by the very structure of the microcable, the invention proposes to transform the distal end of the microcable in a deformable end, able to adapt to various geometries of the deep coronary network and incompressible.

In one embodiment, it is the combination of these two characteristics—deformation and incompressibility—that best addresses the problem of perforation of the coronary vessels while ensuring a better distribution of pressure forces on the walls of the veins than that would be ensured by the single rigid metal sphere coating the strands.

The coating medium can in particular have the shape of a sphere of homogeneous surface, with a diameter between 0.3 and 0.4 mm. According to a particular embodiment, the coating is achieved by fusion of the distal ends of the elementary metal strands. A spherical end enclosing all metal strands is obtained by laser fusion, for example.

To prevent its detachment, the protective cap proximally extends along the core cable in the form of a coating.

In one embodiment, the protective cap is made by a deposit of silicone. Silicone is a biocompatible elastic material, commonly used in medical applications, and in particular, as a component of pacing leads. Silicone can withstand very large deformations and is very slightly compressible.

Finally, an alternative embodiment is that the protective cap comprises a tube of silicone covering the coating means and a distal end carried at the distal end of the silicone tube by silicone adhesive shaping.

In general, the deformable and incompressible material may be a material from the group consisting of: silicones, polyurethanes, polyethers, and copolymers and combinations thereof.

An atraumatic detection/stimulation lead is disclosed. The lead includes at least one microcable having a core cable comprising a plurality of elementary metal strands. One of the microcables has provided at its distal end an atraumatic protection device. The atraumatic protection device includes a protective coating on the distal ends of the elementary strands of the microcable, which may be achieved by melting the distal ends of the elementary strands, and the protective coating is covered by a protective cap of deformable material (which may be both deformable and incompressible). The protective cap may be a conical distal end adapted to deform and axially flatten out. The microcable has an overall diameter less than or equal to 1.5 French (0.50 mm).

A purpose of this invention is to provide a microlead with a microcable structure which would be in conformity with the general requirements for implantable leads as described above, especially the atraumaticity property, thanks to a specific design of the distal end of the microlead to avoid irregularities likely to injure the vein walls. Similarly, the microlead of the invention must meet a number of requirements. In terms of reliability, it is to ensure the flexibility of the end of microcable using biocompatible and very soft materials, while ensuring the functions of electrical stimulation and sealing. The risk of corrosion of the microcable depending on the materials used should also be prevented.

In terms of performance, the requirements are:
Maintain the distal end of the microcable in an overall outside diameter of typically 1.5 French (0.50 mm), to ensure the passage through the deep coronary vessels and in the catheter, and ensuring an isodiameter profile;
Do not alter the flexibility of the distal end of the microlead to maintain maximum maneuverability, including passage through the small veins; and
Facilitate and simplify the implantation method by mastering the progression in the nervous system of the microlead/catheter assembly.

BRIEF DESCRIPTION OF THE DRAWINGS

FIG. 1b is a sectional view of the core cable of the microcable of FIG. 1a.

FIG. 1c is a sectional view of an elementary strand of the core cable of FIG. 1b.

FIG. 2b is a cross section of the microlead of FIG. 2a.

FIG. 3b is a CAD view of FIG. 3a.

FIG. 4b is a CAD view of FIG. 4a.

FIG. 5b is a CAD top view of FIG. 5a.

DETAILED DESCRIPTION

The microleads of the invention are detection/stimulation microleads intended to be implanted in venous, arterial and lymphatic networks. The leads can be either monopolar microleads with a single microcable or multipolar microleads having a plurality of microcables.

In some implementations, these microleads may be intended for cardiac pacing applications, including resynchronization of the cardiac rhythm, which can involve positioning the stimulation electrodes in the coronary venous system, which means veins of small diameter can be reached (and hence it supposes a small thickness). Therefore at least one microcable of the microleads may have an overall diameter of not more than 1.5 French (0.50 mm).

Figure 1A:
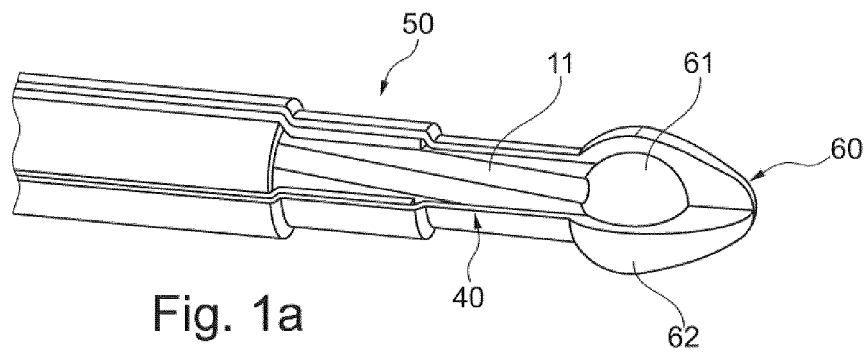
FIG. 1a is a partial perspective view of the distal end of a monopolar microlead with a protective device according to the invention.
Figures 1B, 1C:
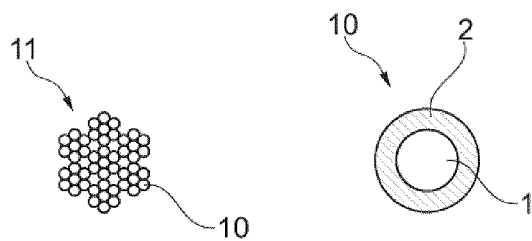

The microlead 50 shown in FIG. 1a is a monopolar microlead with one microcable 40 whose conductor core cable 11, as shown in FIG. 1b, consists of seven intermediate strands of seven elementary metal strands 10 assembled into strands. The diameter of an elementary strand is, for example, 0.033 mm. The diameter of the core cable 11 of the microcable 40 is then 0.3 mm.

FIG. 1c illustrates an elementary strand 10. Strand 10 includes a core 1 in a structural material such as stainless steel, cobalt alloy of the MP35N series, a noble metal, titanium, or a NiTi alloy, of high fatigue resistance, the diameter of 0.033 mm averagely providing a maximum resistance to fatigue tensile strength in the extreme stress conditions to which such structures can be submitted.

Strand 10 may include an amount of radiopaque material 2 in a composite structure providing both fatigue resistance of the cable and radiopacity. Material 2 may be or include any suitable material having X-ray visibility features (e.g., tantalum (Ta), tungsten (W), iridium (Ir), platinum (Pt) and gold (Au)). With modern medical imaging techniques such as MRI, given the small diameter of the strands, this favors heat dissipation and reduces the heating effects of MRI. The thermal energy stored by the material, already limited in volume, can be further reduced if the individual strands are coated with an outer layer of material of low magnetic susceptibility (magnetic susceptibility is the ability of a material to be magnetized by the action of an external magnetic field). The most favorable materials in this application are those whose magnetic susceptibility is less than $2000 \cdot 10\text{-}12 \cdot m^3 \cdot mole^{-1}$, including tantalum (Ta), titanium (Ti), rhodium (Rh), molybdenum (Mo), tungsten (W), palladium (Pd) and gold (Au).

Figure 2A:
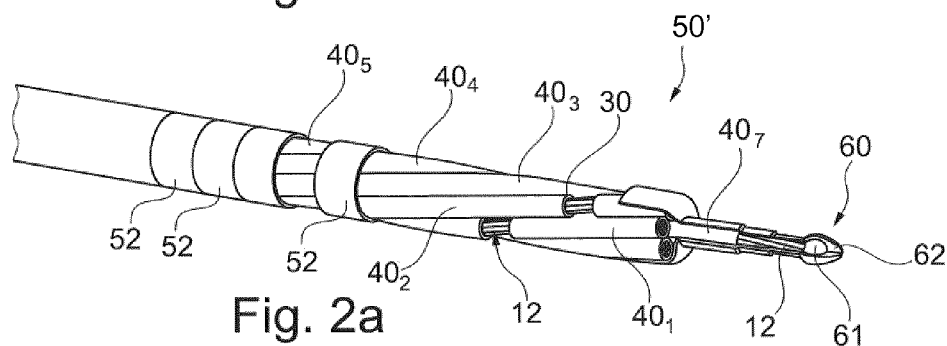
FIG. 2a is a partial perspective view of a multipolar microlead the distal end of a microcable of which bears an atraumatic protection device according to the invention.
Figure 2B:
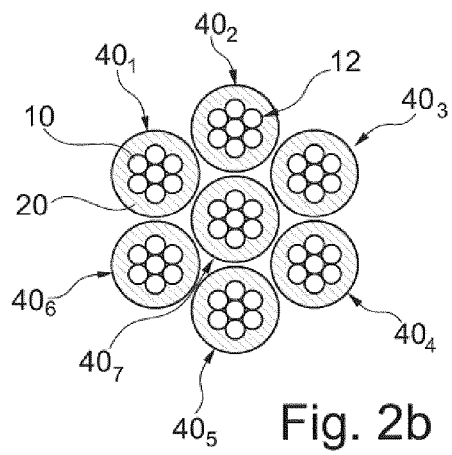

The microlead 50' shown in FIG. 2a is a multipolar microlead and includes a plurality of seven microcables $40_1$, $40_2$, $40_3$, $40_4$, $40_5$, $40_6$, $40_7$ assembled in a strand especially shown in FIG. 2b in cross section, each microcable constituting for the microlead 50' a conduction line connected to a pole of the generator.

As shown in FIG. 2b, a microcable includes a core cable 12 surrounded by an insulation layer 20 so as to provide electrical insulation between the microcables. In the embodiment shown in FIG. 2b, each core cable 12 is formed by a bundle of seven elementary strands 10 having a diameter of also, for example, 0.033 mm. The diameter of a core cable 12 is then 0.1 mm.

To achieve the insulation layer 20, materials with high chemical inertness which also have very good insulation, such as fluoropolymers, may be used. One particular example is ETFE (ethylene tetrafluoroethylene).

As can be seen in FIG. 2a, the insulation layers 20 surrounding the core cables 12 of the microcables have at least an exposed area 30 to form a detection/stimulation electrode for the microlead 50', such as electrodes 52 in FIG. 2a. The exposed areas 30 are notably obtained by laser ablation technique.

In this embodiment, one can observe that the central microcable $40_7$ extends beyond the other microcables of the microlead 50', such that one can install one or more electrodes at its distal end. Of course, the distal end of the microcable 40 of the microlead 50 of FIG. 1a can also be equipped with one or more electrodes.

There may be a risk of perforation of the deep veins of the coronary network due to irregularities that may appear at the distal ends of the microcables during manufacturing. Indeed, the use of a cutter to cut the microcables can lead to the formation of offensive edges (e.g., having pointed and/or sharp angles). One alternative is the use of a laser shot. In this case, the observed risk is that the winding of the strands is damaged and that one or more strands deviate from the nominal isodiameter and become hurtful.

Therefore, as can be seen in FIGS. 1a and 2a, the distal ends 40 and $40_7$ of the microcables that may reach veins of the deep coronary network are equipped with an atraumatic protection device 60. This device 60 essentially consists of two main parts, namely a coating means 61 for the distal ends of the elementary strands of the core cable 11, 12, and a protective cap 62 made of a deformable and incompressible material, wrapping the coating means 61. By its mechanical deformability of incompressibility properties and its biocompatibility, the silicone may be a material of choice for the tip 62.

Figure 3A:
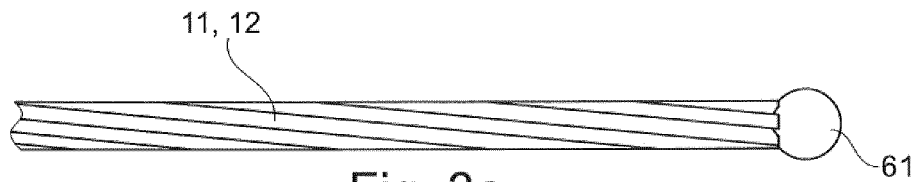
FIG. 3a is a side view of a core cable of a microcable with an encapsulation means of elementary strands.
Figure 3B:
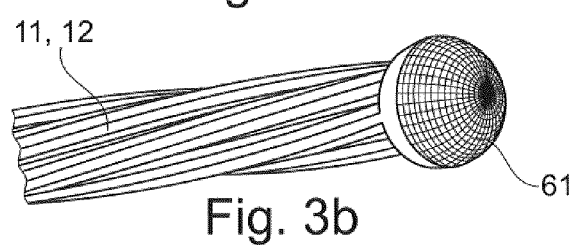

The coating means 61 is designed to eliminate the disadvantages associated with irregularities in the cutting of the microcables. In the embodiment illustrated in FIGS. 3a and 3b, the coating means is made by melting by a laser shot from the distal ends of the elementary metal strands 10 forming the core cables 11, 12. The transformation of the end of the microcable in a homogeneous spherical surface thus eliminates the risk of perforation due to irregularities in the core cables 11, 12.

Figure 4A:
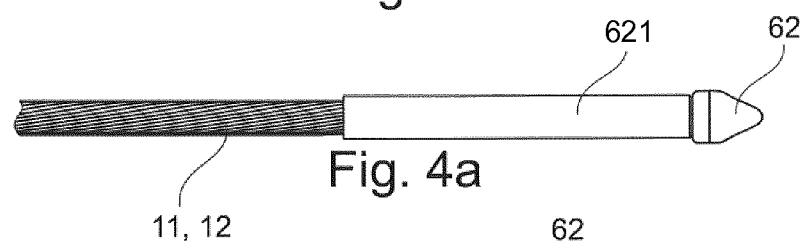
FIG. 4a is a side view of the distal end of a core cable of a microcable with a protection cap.
Figure 4B:
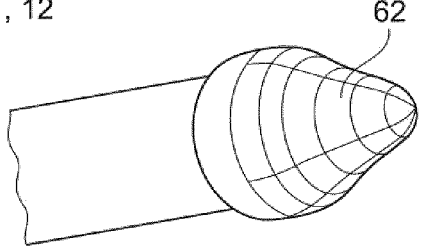
Figure 5A:
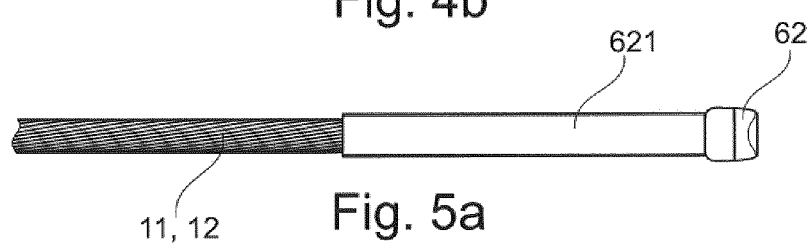
FIG. 5a is a side view of the distal end of the core cable of FIG. 4a whose protective cap is distorted.
Figure 5B:
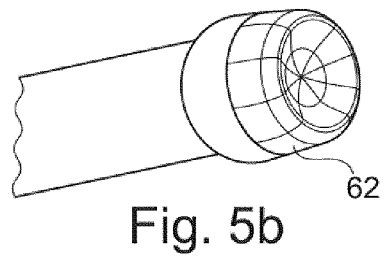

The protective cap 62, shown in FIGS. 4a and 4b with a conical distal end, is intended to address problems related to the rigidity of the metal sphere forming the coating means 61. Indeed, this non-deformable structure cannot adapt the distal end of the microcables to the geometry of deep coronary vessels. The deformability of the tip 62 solves this first problem. Furthermore, the pressures applied by the coating sphere on the venous walls, during insertion of the microlead for example, may be relatively large because the sphere/walls contact surfaces are small. As shown in FIGS. 5a and 5b, the distal end of the tip 62 is able to deform and axially flatten while retaining the area of the contact surfaces. Deformability and incompressibility of the cap 62 ensures that the forces exerted by the physician are spread over a maximum surface area and thus limit the pressure on the walls of the veins.

Note that the metal sphere 61 at the end of the microcable can also mechanically hold the silicone cap 62. To increase the holding force, the protective cap 62 extends along the core cable in the form of a core coating 621. Preferably, the silicone is glued on the entire length of the core coating 621.

Regarding the dimensional aspects, for a monopolar version (with a single microcable as the microcable 40 of FIG. 1a), the sphere 61 may have a diameter between 0.3 and 0.4 mm. So that the tip 62 can move in an implantable catheter of inner diameter 1.6 French (0.53 mm), it is appropriate that the thickness of the silicone cladding is of the order of 0.1 mm or less, or an overall diameter about 0.5 mm, along the length of the cable, and locally of 0.6 mm at the sphere 61, in view of the possibility of local deformation permitted at this location of the silicone sheathing and of the thin catheter tube at the passage of the distal end of the lead.

For a multipolar version (with several microcables $40_1$-$40_7$ as shown in FIG. 2a), only the central $40_7$ microcable of 0.1 mm diameter supports a distal end with the sphere 61 and the silicone cap 62. In this configuration, the thickness of the cover may vary from 0.2 to 0.5 mm maximum, the limitation being that of the passage in the catheter.

Finally, it is contemplated having a steroid such as dexamethasone in the silicone cap 62, for example by mixing silicon powder with dexamethasone, a method commonly used in the manufacture of cardiac leads.

Figure 6:
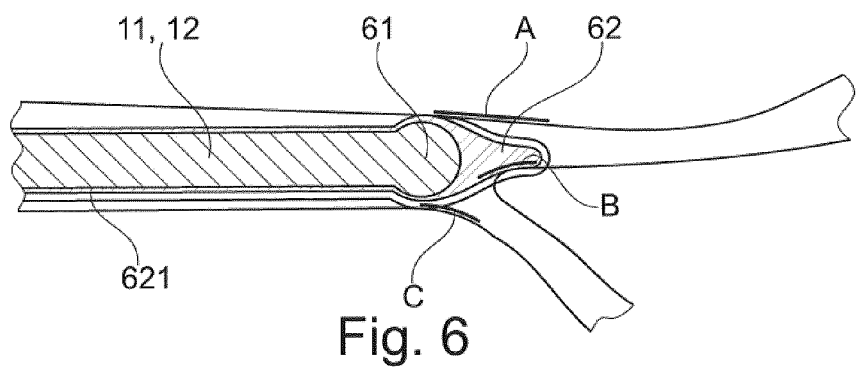
FIG. 6 is a sectional view showing the distal end of the core cable of FIG. 4a stopped in a vein of the deep coronary network.

FIG. 6 illustrates a first example of a situation with a potential risk of perforation wherein the microcable of the microlead faces a vein of reduced diameter.

In the case of a microcable without an atraumatic device, the vein wall alone should withstand the deformation produced by the force exerted by the microlead. The risk of perforation is then dependent on the force applied by the physician and the resistance of the vein walls in contact.

As shown in FIG. 6, the protective cap may help guide the microlead in a vein of the coronary network of smaller diameter, making contact with the walls of the vein and stopping the progression of the microlead. In this case, the area of the silicon surface in contact with the vein wall is preserved, and ensures a better distribution of pressures on the walls (the involved vein surfaces are indicated by the references A, B and C).

Figure 7:
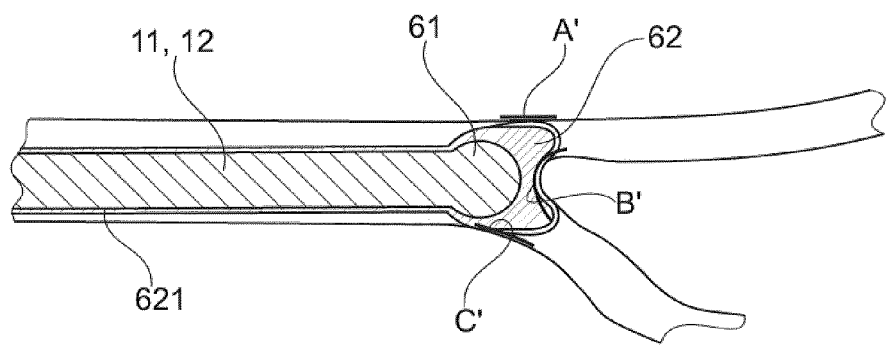
FIG. 7 is a sectional view showing the distal end of the core cable of FIG. 5a stopped against a venous wall of the deep coronary network.

In the example of FIG. 7, the end of the cap 62 is blocked by a front contact with a vein wall of the deep coronary network. The vein and the cap 62 deform to absorb the pressing force. The cap then adopts a distorted geometry as that shown in FIGS. 5a and 5b. The deformation of the silicone defines surfaces A', B' and C' having a total contact area much larger than that corresponding to a microcable departed of the atraumatic system of the invention. The result is again a better distribution of pressures applied to the walls.

Figure 8:
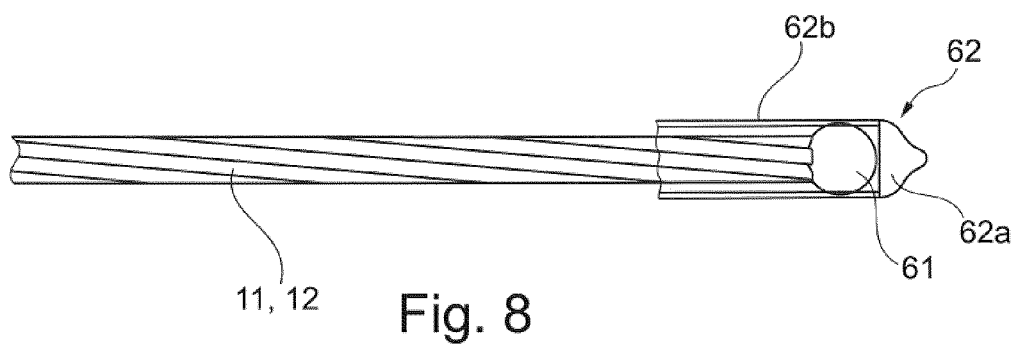
FIG. 8 is a sectional view of an alternative embodiment of the atraumatic protection device according to the invention.

FIG. 8 shows an advantageous embodiment that ensures a constant coating thickness of silicone along the microcable.

In this embodiment, the connector 62 includes a protective silicone tube 62b glued to the core cable 11, 12 and exactly covering the coating metal sphere 61. The deformable geometry in the distal end 62a is formed at the end of the silicone tube 62b, for example by manual conformation of silicone glue.

What is claimed is:

1. A method of manufacturing a lead, comprising:
   constructing a microcable comprising a core cable made of a plurality of elementary metal strands, each having a distal end;
   creating a protective coating on the distal ends of the elementary strands of the core cable; and
   positioning a protective cap of deformable material over the protective coating at a distal end of the core cable.

2. The method of claim 1, wherein the microcable further comprises a plurality of core cables.

3. The method of claim 1, wherein creating the protective coating comprises melting the distal ends of the elementary strands.

4. The method of claim 3, wherein positioning the protective cap comprises fitting the protective cap over a bulbous shape formed by melting the distal ends of the elementary strands.

5. The method of claim 3, wherein positioning the protective cap comprises adhering a length of a core coating sleeve extending from the protective cap along a length the core cable.

6. The method of claim 1, wherein the protective cap is made of a compressible material such that as the protective cap moves into contact with a venous wall, the protective cap can axially flatten to provide a large surface area for distribution of pressure forces on the venous wall.

7. The method of claim 1, wherein the protective coating has the shape of a sphere.

8. The method of claim 7, wherein the diameter of the sphere is between 0.3 mm and 0.4 mm.

9. The method of claim 1, wherein the protective cap is formed from a material that deforms and axially flattens.

10. The method of claim 1, wherein the protective cap is formed by silicone deposition.

11. The method of claim 1, wherein the protective cap comprises a silicone tube covering the protective coating and is secured at a distal end of the silicone tube by silicone adhesive conformation.

12. The method of claim 11, wherein the protective cap and silicon tube provide a constant coating thickness of silicone along the microcable from the tube to the protective cap.

13. The method of claim 12, wherein the silicone tube is glued to the core cable and is sized having a diameter that is substantially the same as the diameter of the protective coating, and wherein a deformable geometry at the distal end is formed at the end of the silicone tube.

14. The method of claim 13, wherein the deformable geometry of the distal end is a conical portion.

15. The method of claim 1, wherein the core cable comprises a plurality of intermediate strands, each of the intermediate strands comprising a plurality of elementary metal strands.

16. The method of claim 1, further comprising surrounding the core cable with an insulation layer.

17. The method of claim 16, wherein the insulation layer surrounding the core cable of the microcable has at least one exposed area to form a detection or a stimulation electrode.

18. The method of claim 1, wherein the lead comprises seven microcables.

19. The method of claim 1, wherein said deformable material is a material from the group consisting of: silicones, polyurethanes, polyethers, and copolymers and combinations thereof.

20. The method of claim 1, wherein the microcable has an overall diameter less than or equal to 1.5 French (0.50 mm).

* * * * *